United States Patent
Zingaretti et al.

(10) Patent No.: US 11,423,318 B2
(45) Date of Patent: Aug. 23, 2022

(54) SYSTEM AND METHODS FOR AGGREGATING FEATURES IN VIDEO FRAMES TO IMPROVE ACCURACY OF AI DETECTION ALGORITHMS

(71) Applicant: DocBot, Inc., Irvine, CA (US)

(72) Inventors: Gabriele Zingaretti, Felton, CA (US); James Requa, Sherman Oaks, CA (US)

(73) Assignee: DocBot, Inc., Irvine, CA (US)

( * ) Notice: Subject to any disclaimer, the term of this patent is extended or adjusted under 35 U.S.C. 154(b) by 0 days.

(21) Appl. No.: 17/473,775

(22) Filed: Sep. 13, 2021

(65) Prior Publication Data

US 2021/0406737 A1    Dec. 30, 2021

Related U.S. Application Data

(63) Continuation-in-part of application No. 16/931,352, filed on Jul. 16, 2020, now Pat. No. 11,191,423, and a continuation-in-part of application No. 16/855,592, filed on Apr. 22, 2020, which is a continuation of
(Continued)

(51) Int. Cl.
| | |
|---|---|
| *G06K 9/00* | (2022.01) |
| *G06N 5/04* | (2006.01) |
| *H04N 19/115* | (2014.01) |
| *G06N 20/00* | (2019.01) |
| *H04N 19/186* | (2014.01) |
| *G06K 9/62* | (2022.01) |
| *G06V 20/40* | (2022.01) |

(52) U.S. Cl.
CPC .............. *G06N 5/04* (2013.01); *G06K 9/6267* (2013.01); *G06N 20/00* (2019.01); *G06V 20/41* (2022.01); *H04N 19/115* (2014.11); *H04N 19/186* (2014.11)

(58) Field of Classification Search
CPC ........ G06N 5/04; G06N 20/00; H04N 19/115; H04N 19/186; G06K 9/00718; G06K 9/6267
See application file for complete search history.

(56) References Cited

U.S. PATENT DOCUMENTS

| | | |
|---|---|---|
| 4,915,435 A | 4/1990 | Levine |
| 6,082,799 A | 7/2000 | Marek |
| 6,171,112 B1 | 1/2001 | Clark et al. |
| (Continued) | | |

FOREIGN PATENT DOCUMENTS

WO    WO-2021010985 A1    1/2021

OTHER PUBLICATIONS

Anderson et al., "Prepared by ASGE Standards of Practice Committee," Endoscopy by Nonphysicians, Gastrointestinal Endoscopy, vol. 69(4), 2009, pp. 767-771.
(Continued)

*Primary Examiner* — Avinash Yentrapati
(74) *Attorney, Agent, or Firm* — Eversheds Sutherland (US) LLP; Nicola A. Pisano; Albert K. Heng

(57) ABSTRACT

Methods and systems are provided for aggregating features in multiple video frames to enhance tissue abnormality detection algorithms, wherein a first detection algorithm identifies an abnormality and aggregates adjacent video frames to create a more complete image for analysis by an artificial intelligence detection algorithm, the aggregation occurring in real time as the medical procedure is being performed.

18 Claims, 4 Drawing Sheets

Related U.S. Application Data application No. 16/512,751, filed on Jul. 16, 2019, now Pat. No. 10,671,934.

(56) References Cited

U.S. PATENT DOCUMENTS

| | | | |
|---|---|---|---|
| 6,246,784 B1* | 6/2001 | Summers | G06K 9/00201 382/128 |
| 6,928,314 B1 | 8/2005 | Johnson et al. | |
| 7,011,625 B1 | 3/2006 | Shar | |
| 7,454,045 B2* | 11/2008 | Yao | G06K 9/00201 382/128 |
| 7,583,831 B2* | 9/2009 | Tu | G06K 9/38 382/131 |
| 7,914,442 B1 | 3/2011 | Gazdzinski | |
| 8,165,358 B2 | 4/2012 | Sirohey et al. | |
| 8,965,108 B2* | 2/2015 | Chabanas | G06T 7/149 382/154 |
| 9,224,193 B2 | 12/2015 | Tsujimoto | |
| 10,606,982 B2 | 3/2020 | Guo et al. | |
| 10,671,934 B1 | 6/2020 | Ninh et al. | |
| 10,682,108 B1 | 6/2020 | Ma et al. | |
| 11,191,423 B1* | 12/2021 | Zingaretti | G06T 7/0016 |
| 2002/0097320 A1* | 7/2002 | Zalis | G06T 7/12 348/65 |
| 2003/0132936 A1* | 7/2003 | Kreeger | G06T 7/0012 345/420 |
| 2004/0249670 A1 | 12/2004 | Noguchi et al. | |
| 2005/0036668 A1 | 2/2005 | McLennan et al. | |
| 2005/0078858 A1* | 4/2005 | Yao | G06T 7/149 382/128 |
| 2005/0117787 A1 | 6/2005 | Iordanescu et al. | |
| 2007/0003131 A1 | 1/2007 | Kaufman | |
| 2007/0005795 A1 | 1/2007 | Gonzalez | |
| 2007/0103464 A1 | 5/2007 | Kaufman et al. | |
| 2007/0265492 A1 | 11/2007 | Sonnenschein et al. | |
| 2007/0279521 A1 | 12/2007 | Cohen | |
| 2008/0058593 A1* | 3/2008 | Gu | G06T 7/0012 600/109 |
| 2009/0063118 A1 | 3/2009 | Dachille et al. | |
| 2010/0097392 A1* | 4/2010 | Nishiyama | A61B 1/041 345/593 |
| 2010/0194851 A1 | 8/2010 | Pasupaleti et al. | |
| 2010/0215226 A1* | 8/2010 | Kaufman | G06V 10/267 382/128 |
| 2011/0063288 A1* | 3/2011 | Valadez | G06T 15/08 345/419 |
| 2011/0187707 A1 | 8/2011 | Kaufman et al. | |
| 2011/0301447 A1* | 12/2011 | Park | G06T 7/0016 600/407 |
| 2012/0320088 A1 | 12/2012 | Ihara et al. | |
| 2013/0033419 A1* | 2/2013 | Dror | G06T 7/174 345/156 |
| 2013/0077838 A1* | 3/2013 | Lamash | G06T 7/41 382/128 |
| 2013/0170726 A1 | 7/2013 | Kaufman et al. | |
| 2014/0031677 A1 | 1/2014 | Iftimia et al. | |
| 2014/0233826 A1* | 8/2014 | Agaian | G06K 9/46 382/133 |
| 2015/0106123 A1 | 4/2015 | Amarasingham et al. | |
| 2015/0260534 A1 | 9/2015 | Shen | |
| 2015/0282749 A1 | 10/2015 | Zand et al. | |
| 2015/0374210 A1 | 12/2015 | Durr et al. | |
| 2016/0027184 A1* | 1/2016 | Courtney | G06T 7/0012 345/424 |
| 2016/0163048 A1* | 6/2016 | Yee | G06F 3/04845 382/131 |
| 2016/0210411 A1 | 7/2016 | Mentis | |
| 2016/0364526 A1 | 12/2016 | Reicher et al. | |
| 2018/0225820 A1* | 8/2018 | Liang | G16H 50/20 |
| 2018/0247405 A1* | 8/2018 | Kisilev | A61B 5/0013 |
| 2018/0253839 A1* | 9/2018 | Zur | A61B 1/000094 |
| 2019/0238791 A1 | 8/2019 | Ingle | |
| 2019/0244351 A1* | 8/2019 | Dolnik | A61B 5/42 |
| 2019/0282190 A1* | 9/2019 | Dargis | G06T 7/11 |
| 2019/0289359 A1 | 9/2019 | Sekar et al. | |
| 2019/0297276 A1* | 9/2019 | Sachdev | A61B 1/000096 |
| 2019/0311474 A1* | 10/2019 | Angermann | G06K 9/6292 |
| 2019/0370963 A1 | 12/2019 | Chiu et al. | |
| 2019/0392942 A1 | 12/2019 | Sorenson et al. | |
| 2020/0387706 A1* | 12/2020 | Zur | G06K 9/6271 |
| 2021/0133964 A1* | 5/2021 | Sachdev | G16H 30/40 |
| 2021/0158526 A1* | 5/2021 | Patil | G06N 3/08 |
| 2021/0274089 A1* | 9/2021 | Wang | H04N 5/23238 |
| 2021/0342592 A1* | 11/2021 | Oosake | G06K 9/6232 |
| 2021/0345865 A1* | 11/2021 | Spillinger | A61B 1/00 |

OTHER PUBLICATIONS

Corley DA., et al., "Adenoma Detection Rate and Risk of Colorectal Cancer and Death," New England Journal of Medicine, vol. 370, 2014, pp. 1298-1306.

Day L.W., et al., "Non-Physician Performance of Lower and Upper Endoscopy: A Systematic Review and Meta-Analysis," Endoscopy, vol. 46 (5), May 2014, pp. 401-410.

Desai, et al., An Adaptive Supervision Framework for Active Learning in Object Detection, arXivpreprint arXiv: 1908.02454 (Aug. 2019).

Greenwald Z.R., et al., "Mobile Screening Units for the Early Detection of Cancer: A Systematic Review," Cancer Epidemiol. Biomarkers Prev., vol. 26(12), 2017, pp. 1679-1694.

Holmes T., "What Is Frame Rate?" Feb. 2019, pp. 2, Retrieved from the Internet: URL: https://wistia.com/learn/production/what-is-frame-rate).

International Search Report and Written Opinion dated Oct. 9, 2019 in Int'l. PCT Patent Appl. Serial No. PCT/US2019/041945.

Kaminski M.F., et al., "Quality Indicators for Colonoscopy and the Risk of Interval Cancer," New England Journal of Medicine, vol. 362, 2010, pp. 1795-1803.

Karnes W.E., et al., "Su1642 Automated Polyp Detection Using Deep learning: Leveling the Field," Gastrointestinal Endoscopy, Supplement, vol. 85(5), 2017, pp. AB376-AB377.

Komaravolu S.S., et al., "Colonoscopy Utilization in Rural Areas by General Surgeons: An Analysis of the National Ambulatory Medical Care Survey," The American Journal of Surgery, vol. 218(2), 2019, pp. 281-287.

Mohammed, et al., PS-DeVCEM: Pathology-sensitive deep learning model for video capsule endoscopy based on weakly labeled data, Computer Vision and Image Understanding, 201:103062 (Dec. 2020).

Riegert M.L., et al., "Experience of a Nurse Practitioner Performing Colonoscopy at a Tertiary Center in the United States," Journal of Gastrointestinal & Digestive System, vol. 5, 2015, p. 3.

Sani, et al., A Comparison of the Efficacy, Adverse Effects, and Patient Compliance of the Sena-Graph™ Syrup and Castor Oil Regimens for Bowel Preparation, Iranian Journal of Pharmaceutical Research, 9(2):193-198 (2010).

Talukdar R., et al., "Making Endoscopy Mobile: The Journey," Digestive Endoscopy, vol. 24, Suppl. 1, May 2012, pp. 172-174.

Urban G., et al., "Deep Learning Localizes and Identifies Polyps in Real Time With 96% Accuracy in Screening Colonoscopy," Gastroenterology, vol. 155 (4), Oct. 2018, pp. 1069-1078.

Varayil, et al., Colonoscopy: What Endoscopists Inspect Under Optimal Conditions, Gastroenterology, 5(140):S-718 (2011).

Wang P., et al., "Real-Time Automatic Detection System Increases Colonoscopic Polyp and Adenoma Detection Rates: A Prospective Randomized Controlled Study," Gut, vol. 68, No. 10, Oct. 2019, pp. 1813-1819.

Zachariah R., et al., "Artificial Intelligence for Colon Polyp Detection: Why Should We Embrace This?" Techniques and Innovations in Gastrointestinal Endoscopy 22, 2020, pp. 48-51.

Zachariah R., et al., "Can Artificial Intelligence (AI) Achieve Real-Time Reset and Discard' Thresholds Independently of Device of Operator?" American Journal of Gastroenterology, vol. 113, 2018, p. S129.

(56) References Cited

OTHER PUBLICATIONS

International Search Report & Written Opinion dated Oct. 15, 2021 in Int'l PCT Patent Appl. Serial No. PCT/US2021/039009 (0310).

* cited by examiner

US 11,423,318 B2

SYSTEM AND METHODS FOR AGGREGATING FEATURES IN VIDEO FRAMES TO IMPROVE ACCURACY OF AI DETECTION ALGORITHMS

I. REFERENCE TO RELATED APPLICATIONS

This application is a continuation-in-part of co-pending U.S. patent application Ser. No. 16/855,592, filed Apr. 22, 2020, which is a continuation application of U.S. patent application Ser. No. 16/512,751, filed Jul. 16, 2019, now U.S. Pat. No. 10,671,934, the entire contents each of which are incorporated herein by reference. This application is also a continuation-in-part application of U.S. patent application Ser. No. 16/931,352, filed Jun. 16, 2020, the entire contents of which are incorporated herein by reference.

II. FIELD OF THE INVENTION

This invention relates generally to the field of real-time imaging of a body cavity, with particular application to endoscopy such as colonoscopy and upper endoscopy.

III. BACKGROUND OF THE INVENTION

Endoscopy refers to a medical procedure in which an instrument is used for visual examination of an internal body part. A common example of endoscopy is colonoscopy, during which a flexible tube with imaging apparatus at the distal end is inserted into a person's colon. The purpose of colonoscopy is to search for and identify abnormalities in the internal wall of the colon and, in some cases, remove them. Such abnormalities include polyps and adenomas of several types.

Barrett's esophagus is a condition in which the lining of the esophagus changes, becoming more like the lining of the small intestine rather than the esophagus. This occurs in the area where the esophagus is joined to the stomach. Endoscopy is used in the esophagus as part of the clinical examination in cases of suspected Barrett's esophagus.

Endoscopic procedures for other organs (e.g.: the bronchial tree) have similar characteristics, and the invention disclosed herein has applicability to other endoscopic procedures.

Screening colonoscopy remains the best proven method to prevent colon cancer. Clinical guidelines typically suggest that a first colonoscopy be performed at age 50. In screening colonoscopy, the colonoscopist performs a rigorous visual examination of the entire internal lining of the colon, looking for abnormalities such as polyps and adenomas. Polyps within certain parameters are often removed during the same procedure.

Endoscopy such as colonoscopy is typically performed by a fellowship-trained gastroenterologist. Colonoscopy also is performed by primary care physicians (PCP), general surgeons, nurse practitioners and physician assistants. In this disclosure, each person performing a colonoscopy is referred to as an endoscopist.

A well-accepted measure of quality of colonoscopy is the so-called "adenoma detection rate" (or ADR). This is a measure of the proportion of patients receiving a colonoscopy in whom an adenoma is detected. ADR is a proven measure of risk of colorectal cancer between screenings ("interval colorectal cancer") and the ADR is inversely associated with the risks of interval cancer (Kaminski M. F. et al "quality Indicator for Colonoscopy and the Risk of Interval Cancer" NEJM 2010; 362:1795-803).

The prevalence of adenomas in the screening age population is thought to be about 50% (i.e.: half of people screened have at least one adenoma), but typical ADR is about 25% (Corley D. A. et al "Adenoma Detection Rate and Risk of Colorectal Cancer and Death" NEJM 2014; 370: 1298-306). This means that about half of screened patients have an adenoma that is missed. There are several factors that contribute to lower than ideal ADR. One factor is the difficulty of identifying a polyp or adenoma, even though it may be in the visual field of the colonoscopy image.

Another factor that contributes to the lower than ideal ADR is the difficulty of ensuring that the entire internal surface of the colon has been imaged. It is difficult for a colonoscopist to remember what has been imaged, and "integrate" those images mentally to conclude that the entire internal surface has been looked at, and thus it is extremely challenging for the endoscopist to assure that the entire internal surface of the colon has been visualized. Failure to visualize the entire internal surface incurs a risk of missing potentially harmful polyps or cancers. On average, only about 81% of the colon mucosa is visualized in a colonoscopy, even under optimal conditions (Eddakanambeth, V J, Enders, F, Tavanapong, W, Oh, J, Wong, J, and de Groen, P C. "Colonoscopy what endoscopists inspect under optimal conditions." Digestive Disease Week 2011, Chicago, Ill.).

In recent years, Artificial Intelligence (AI) has been used to help the endoscopist. One of the challenges of using AI for endoscopy is that because of the large variance in tissue, anatomy and motion dynamics during the procedure, the AI must be trained over a very large set of data which can be hard to collect.

Another challenge is that previously-known AI processes the video feed in real time, and thus operates prospectively during a procedure. Accordingly, the AI only can analyze the data as it is fed to its algorithms, i.e., process information on a per frame basis. The AI has no historical memory of the frames before the frame currently being analyzed, but instead processes each frame independently.

Another challenge in endoscopy with AI is that the tip of the endoscope is controlled by a series of knobs and switches located on the end piece held and manipulated by the endoscopist. However, the endoscopist's attention is focused on the screen (or monitor) and not the controls. It is quite difficult for many people to correlate the image on the screen into hand movements necessary to direct the tip of the endoscope. Hence, control reference between the tip of the endoscope and the series of controls on the handpiece often is lost. This means many frames fed to the AI technology are ultimately not useful or carry very little information. Further, some of the frames may contain only partial information that limits the extraction capability of the AI algorithms.

Due to shortcomings in current endoscopic technology, the quality of the procedure is highly influenced by the dexterity of the endoscopist. The way the endoscope is used directly correlates with the quality of images available for the AI to analyze in real time.

Quite often the AI algorithms must characterize areas of interest with limited spatial and temporal information. "Temporal information" means the area of interest only may be visible for a short period of time. "Spatial information" means the entirely of the area of interest may be not visible and/or may be partially obstructed. Furthermore, said spatial and temporal information me be available at different times, e.g., portion P1 of an adenoma is visible only at time T1 and portion P2 of the adenoma is visible only at time T2. In such circumstances, while the AI may be programmed to try to best characterize the information provided at T1 and T2, at neither time would it have the complete image of P1+P2. Accordingly, the AI may not be able to detect the entire abnormality in a single frame.

Image stacking has been used in many different disciplines to provide higher resolution and quality images from a single source. One example of image stacking is used in microscopic photography where, to capture very small details of a subject, special lenses are used that provide macro-level imaging with a concomitantly narrow depth of field. In this case, to capture an entire subject of interest, multiple pictures are taken of several areas of the subject. Portions of the pictures out of focus then are removed and the resulting subpictures are stitched together to ultimately compile the final macro picture.

Panoramic pictures are yet another example in which multiple images are stitched together. Although a wide angle lens provides a wide field of view, e.g., suited for outdoor photography, such lenses also introduce a high degree of distortion at the periphery. It is common practice to use a lens with very minimal distortion, pan the camera along an axis and then stitch the images together to compile a large panoramic image.

Another example in which multiple number of slices are stitched together is 3D volume reconstruction or volume rendering to create a 3D volume. One drawback of this approach is that the algorithm has no knowledge if it is stitching together images that belong to the same object or different objects. It is therefore up to the operator to make sure the stitching is done properly, with all the images belonging to the same object. In addition, none of the foregoing methods operate in real time, but rather require post-processing of the information. Accordingly, none are suitable for real time applications, such as endoscopy.

U.S. Patent Application Publication No. US 2010/0194851 to Pasupaleti et al. describes a system and method of stitching together multiple images to create a panoramic image by registering the images by spatial relationship. This application describes that the images preferably taken on the same plane and stitched together by overlapping common portions of adjacent images. This application does not address the problems that arise when attempting to stitch together images taken on different focal planes that provide only partial information of an object.

U.S. Pat. No. 9,224,193 to Tsujimoto et al. describes an image processing apparatus for stacking images on the Z axis. This method employs specialized hardware as well as image processing algorithms for computing depth of field, focus and blur detection. The patent does not address features extraction and stacking images based on similarity of the extracted features.

In view of the foregoing drawbacks of previously known systems, it would be desirable to provide a method of recognizing that a portion of an area of interest in a current frame belongs to the same area of interest at a previous time, such that the method sums all of the subareas and analyzes the subareas together.

Furthermore, as the endoscopist continues to examine the area of interest, the AI algorithm may analyze additional information to ultimately compile a full data picture for the tissue under examination, as supposed to an instantaneous partial picture.

It therefore would be desirable to provide a system having an AI system for use with endoscopic modalities, such as colonoscopy or upper endoscopy, wherein the AI system is directed to combine multiple portions of an area of interest for analysis in real time.

IV. SUMMARY OF THE INVENTION

The systems and methods of the present invention enable an AI system to recognize and group portions of an area of interest in a multiple video frames generated by an endoscope, thereby enabling analysis of the subareas the multiple video frames together. In this manner, as an endoscopist continues to examine an area of interest, the AI algorithm is able to analyze additional information to ultimately compile a full data picture for the tissue under examination.

The inventive system and methods further provide an AI system for use with endoscopic modalities, such as colonoscopy or upper endoscopy, wherein the AI system is directed to combine multiple portions of an area of interest for analysis in real time. While this disclosure describes the present invention in the context of colonoscopy, as just one example of it application in the field of endoscopy, it should be appreciated by persons of skill in the art that the invention described herein has applicability to multiple other forms of endoscopy.

In accordance with one aspect of the invention, systems and methods are provided for generating high quality images for submission to AI detection algorithms used in endoscopic medical procedures, to thereby yield better outcomes. The inventive systems and methods are expected to provide essentially seamless performance, as if the AI detection algorithms were running in their canonical form.

In one embodiment, the system provides multiple display windows, preferably at least two display windows. The first display window displays real time images of the procedure to the endoscopist as the examination, is being performed, for example, as in conventional colonoscopy. The first display window also displays information from an automatic detection system, for example, bounding boxes, overlaid on real-time images of polyps and other abnormalities detected in the video stream images from the endoscopy machine. The second display window displays at an evolving view of a stitched area of interest. As the AI module detects an area of interest shown in the first monitor display and the endoscopist explores that area, the second screen will update the information in real time by stitching together multiple images and features of the area of interest. As the endoscopist maneuvers the endoscope to redirect it within the area of interest, a visual indicator will display the updated information regarding detected tissue features or abnormalities. For example, if a lot of information is added in the stitched image, a red indicator may slowly transition to green (or any other color) as the accumulated information (or features) are adjudged by the AI module to become less likely to contain areas of concern.

As colonoscopy is an imaging technique that affords limited anatomical guidance, it is not uncommon for the endoscopist to become spatially disoriented regarding the precise location of the anatomy under examination. When this happens, it is possible for the endoscope to become oriented in a way that is physically difficult to unwind, thereby resulting in limited view of the anatomy and limiting the quality of data provided to the AI module for a specific area or lesion. In accordance with another aspect of the invention, the inventive software may guide the endoscopist where to next move the endoscope to collect additional information for processing by the AI module and to further visualize the area of interest.

Display of the first and the second display windows may be performed in a parallel or as a multi-threaded process. Parallel processing advantageously allows the system to display the video data received from the endoscope in real-time, and also display the graphical indications in the second window at a frame rate that may be lower than or equal to the frame rate of the first window. In this manner, the present invention provides visual clues that improve the quality and quantity of the information provided to the detection algorithms. Systems constructed in accordance with the inventive principles also enable the detection algorithm to determine if there are enough features extracted based on the real time images available to assess an area under examination, or if more data is required, thereby greatly improve the efficacy of the detection algorithms.

Further areas of applicability of the present disclosure will become apparent from the detailed description, the claims and the drawings. The detailed description and specific examples are intended for illustration only and are not intended to limit the scope of the disclosure.

V. BRIEF DESCRIPTION OF THE DRAWINGS

VI. DETAILED DESCRIPTION OF THE INVENTION

The present invention is directed to systems and methods for analyzing multiple video frames imaged by an endoscope with an artificial intelligence ("AI") software module running on a general purpose or purpose-built computer to aggregate information about a potential tissue feature or abnormality, and to indicate to the endoscopist the location and extent of that feature or abnormality on a display viewed by the endoscopist. In accordance with the principles of the present invention, the AI module is programmed to make a preliminary prediction based on initially available information within a video frame, to aggregate additional information for a feature from additional frames, and preferably, to provide guidance to the endoscopist to direct him or her to move the imaging end of the endoscope to gather additional video frames that will enhance the AI module detection prediction.

Figure 1:
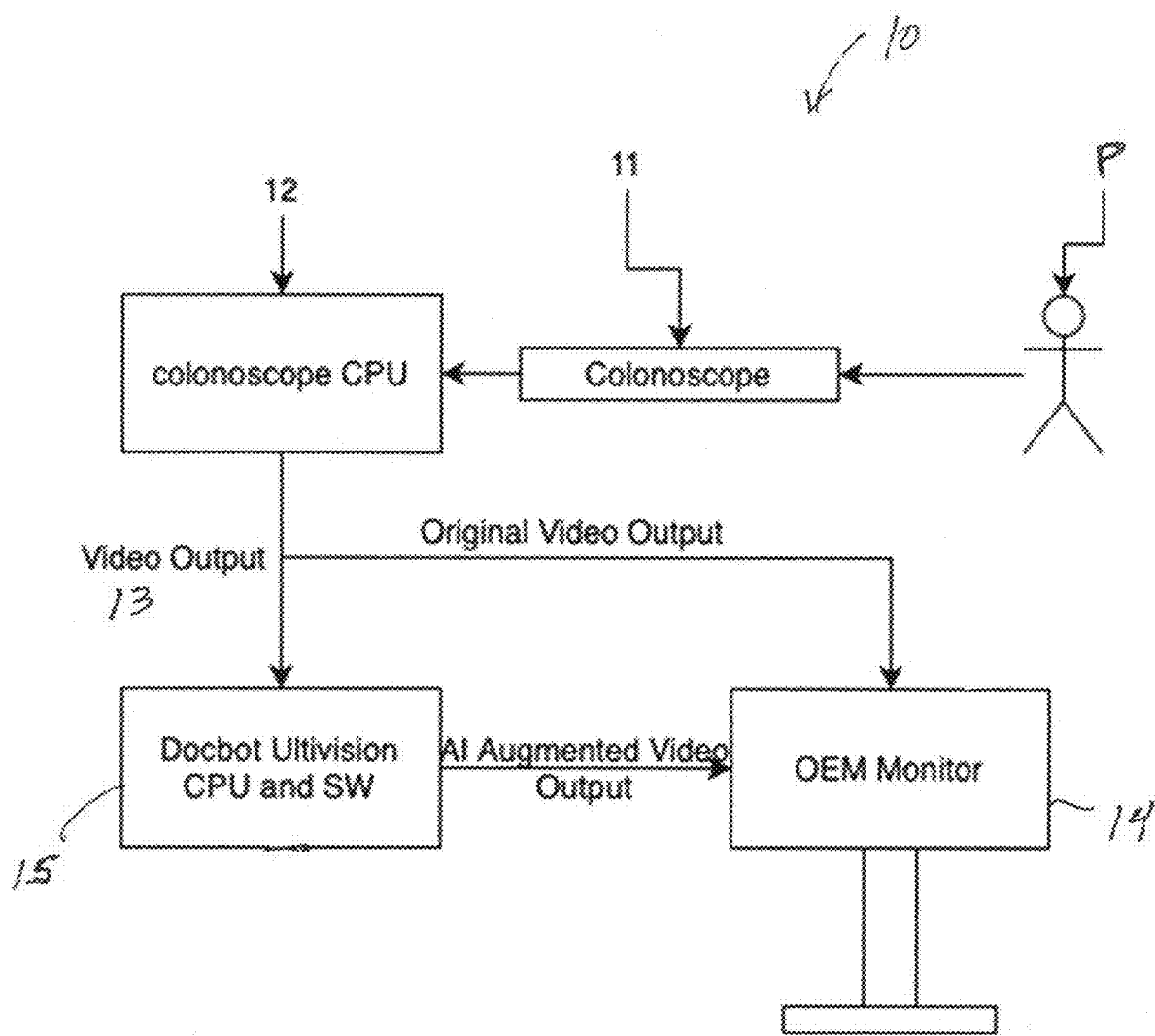
FIG. 1 is a schematic depicting an exemplary configuration of a system incorporating the principles of the present invention.

Referring to FIG. 1, exemplary colonoscopy system 10 configured in accordance with the principles of the present invention is described. Patient P may be lying on an examination table (not shown) for a colonoscopy procedure using conventional colonoscope 11 and associated colonoscope CPU 12, which receives the image signals from the camera on board colonoscope 11 and generates video output 13, which may be displayed on monitor 14 located so as to be visible to the endoscopist. Video output 13 also is provided to computer 15, which is programmed with an AI module configured in accordance with the principles of the present invention as described below. Computer 15, which may be a general purpose or purpose-built computer, includes one of more processors, volatile and non-volatile memory, input and output ports, and is programmed to process video output 13 to generate AI augmented video output 16. The details of a colonoscopy procedure, including patient preparation and examination, and manipulation of colonoscope are well known to those skilled in the art.

Colonoscope 11 acquires real-time video of the interior of the patient's colon and large intestine from a camera disposed at the distal tip of the colonoscope once it is inserted in the patient. Data from colonoscope 11, including real-time video, is processed by computer to generate video output 13. As shown in FIG. 1, one output of computer 12 displayed in a first window on monitor 14 as real-time video of the colonoscopy procedure. Video output 13 also is provided to computer 15, which preferably generates an overlay on the video indicating areas of interest detected in displayed image identified by the inventive AI module running on computer 14, e.g., a polyp, lesion or tissue abnormality. In accordance with one aspect of the present invention, computer 15 also may display in a second window on monitor 14 information about the area of interest and the quality of the aggregated frames analyzed by the AI module to identify the area of interest. The AI software module running on computer 15 may be of many types, but preferably includes artificial intelligence decision-making ability and machine learning capability.

Figure 2:
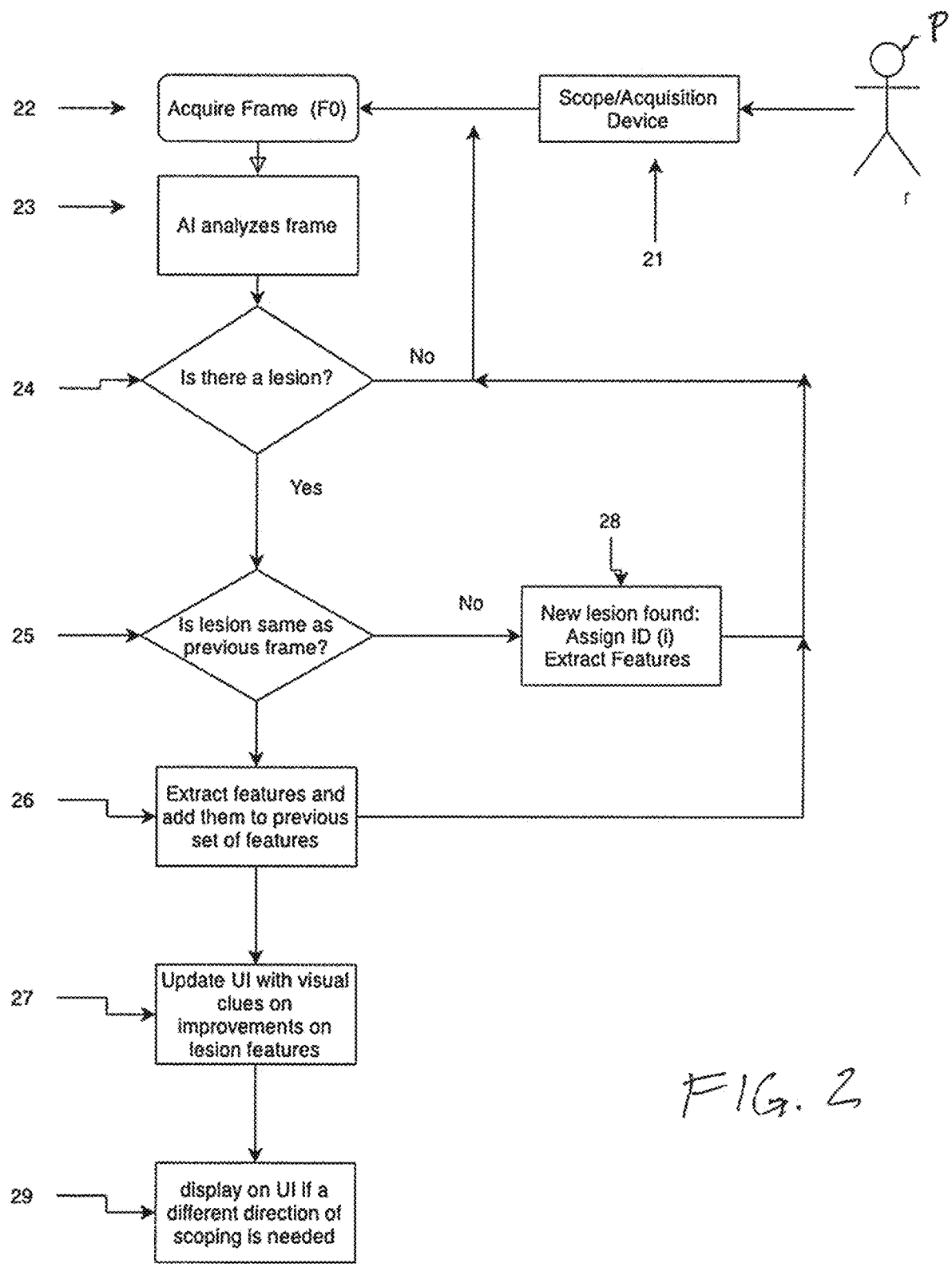
FIG. 2 is an exemplary flowchart depicting data processing in the inventive system.

Referring now to FIG. 2, information flow in the inventive system is described. Video data captured from by a colonoscope of the interior of colon and large intestine of patient P is processed by colonoscopy computer 21 (corresponding to components 11 and 12 of FIG. 1). Each video frame from the live video feed is sent to computer 15 of FIG. 1, which performs steps 22-29 of FIG. 2. In particular, each video frame, labelled $F_0$, from colonoscopy machine 21 is acquired at step 22 and analyzed by the processor of computer 15 at step 23. If the AI module detects a lesion at step 24 ("Yes" branch from decision box 24), additional frames of the video stream are analyzed, at step 25, to determine if the lesion is the same lesion as identified in the previous video frame. If the lesion in the current frame is determined to be a new lesion than previously identified ("No" branch from decision box 25), a new identifier ("ID") is assigned to that new lesion at step 28 and additional frames are analyzed to extract data for that new lesion.

If at step 25 the lesion in the additional video frames is adjudged to be the same lesion identified in previous frames, at step 25, features for the lesion are extracted and aggregated by combining information from the previous frame with information from the new frame at step 26. The AI module then reanalyzes the aggregated data for the lesion and updates its detection prediction analysis, at step 27. Specifically, at step 26, the software extracts features from the current video frame and compares that data with previously detected features for that same lesion. If the newly extracted data from the current frames add additional detail, that information then is combined together with the data from the prior frame or frames. If the AI module determines that additional images are required, it may issue directions, via the second window, to reposition the colonoscope camera to obtain additional video frames for analysis at step 29. Further details of that process are described below with respect to FIG. 4.

The foregoing process described with respect to FIG. 2 is similar to analogous to stitching together multiple adjacent or overlapping images to form a panoramic image. In this case, however, the aggregation is done algorithmically, using the AI module, to analyze images derived from different planes and/or different angles, rather than a single plane as would commonly be the case for panoramic imaging or macroscopic photography. In addition, because the additional video frames adding more information to about the previous detection for the same areas of interest, the AI module does not simply analyze the new information from the newly acquired frame, but instead preferably reanalyzes the lesion detection prediction using all of the available information, including the current and past video frames, and thus is expected to provide greater detection accuracy.

Still referring to FIG. 2, once the AI module has analyzed the aggregated data at step 27, it may display in the second display window a progress indicator that informs the endoscopist regarding how much data has been aggregated and analyzed. This indicator will aid the endoscopist in assessing whether additional effort should be made to examine an area of interest, thus yielding more data for the AI module and potentially improving the examination procedure. As noted above, the AI module, at step 29, also could suggest a direction to move the endoscope to collect additional information needed to complete the analysis of an area of interest, for example, by displaying directional arrows or text.

In one preferred embodiment, the AI module may use landmarks identified by a machine learning algorithm to provide registration of images between multiple frames. Such anatomical landmarks may include tissue folds, discolored areas of tissue, blood vessels, polyps, ulcers or scars. Such landmarks may be used by the feature extraction algorithms, at step 26, to help determine if the new image(s) provide additional information for analysis or may be used at step 25 to determine whether a current lesion is the same lesion as the a previous frame or a new lesion, which is assigned a new identifier at step 28.

Figure 3:
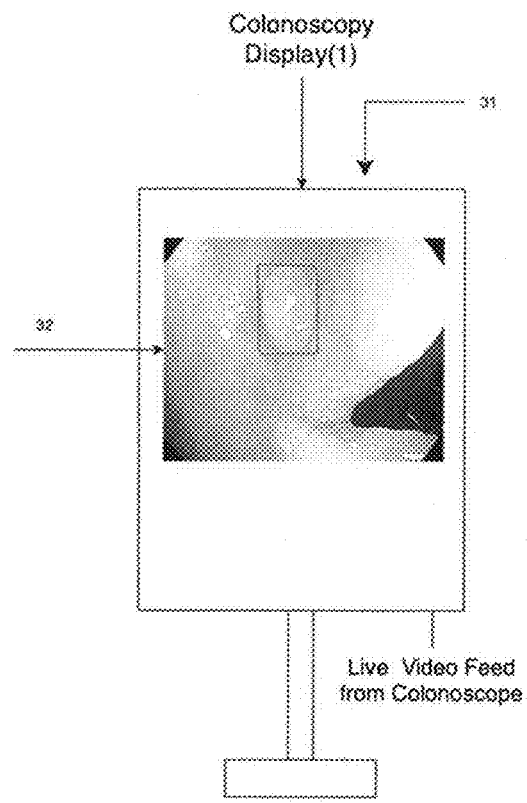
FIG. 3 is a schematic depicting how an endoscopist might see a display screen showing just frame-based AI module detection predictions.

Referring now to FIG. 3, monitor 31 displays a live feed from the colonoscope along with a real time frame-based AI module detection prediction 32, as described, for example in commonly assigned U.S. Pat. No. 10,67,934, the entirety of which is incorporated herein by reference. The display shows the real time video output of the colonoscope including bounding box 33 determined as an output of an AI module that highlights an area of interest as potentially including a tissue feature or lesion for the endoscopist's attention. In accordance with the principles of the present invention, the AI module prediction accuracy is enhanced by including multiple video frames of the same tissue feature or lesion in the analysis, and by directing the endoscopist to redirect the camera of the endoscope to obtain further images of an area of interest.

Figure 4:
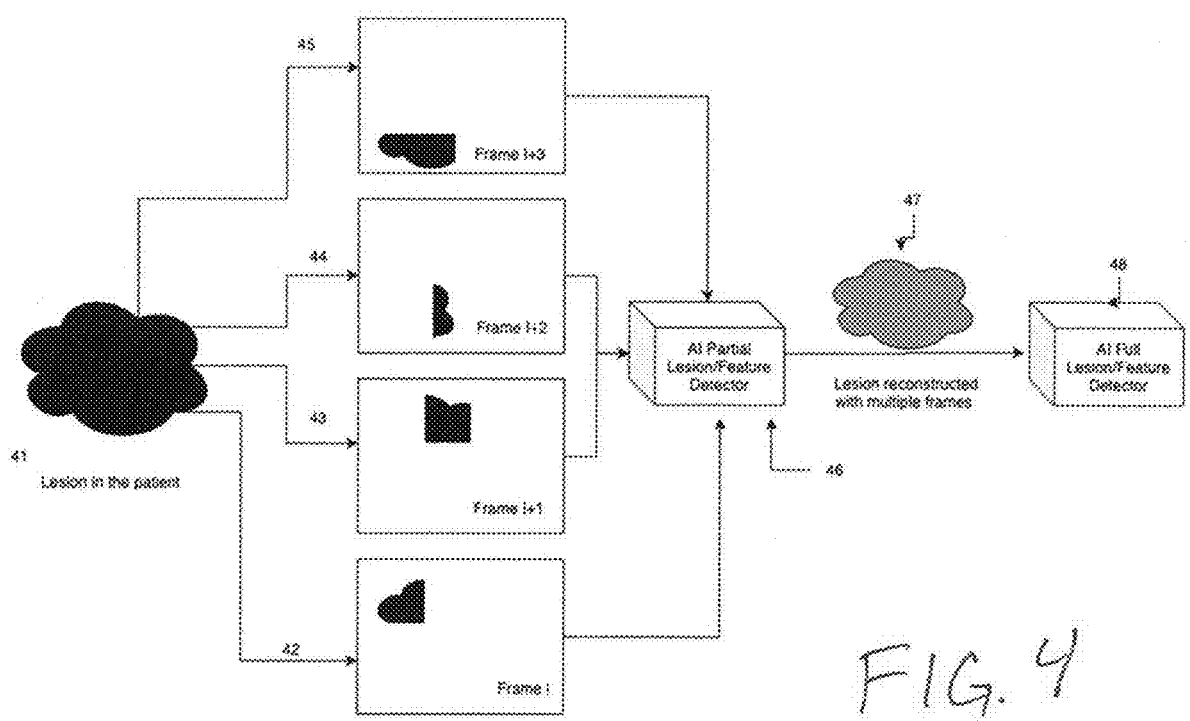
FIG. 4 depicts how an AI module configured in accordance with the principles of the present invention combines information for a single lesion over multiple frames.

With respect to FIG. 4, operation of the AI module to aggregate data from additional video frames is now described. A lesion in real life is a three dimensional body. Due to the limitations of camera technology, the three-dimensional interior tissue wall of a colon and large intestine of a patient will be seen in a two dimensional space projected. The type of image acquired by the colonoscope camera therefore is highly dependent on the ability of the endoscopist to manipulate the colonoscope. Accordingly, a single lesion may be only partially visible in one or multiple frames. In accordance with the present invention, however, the AI module is programmed to analyze each frame of the video stream to extract particular features of an area of interest, e.g., a lesion or polyp, to reconstruct a higher quality representation of the lesion that then may be analyzed by detection and characterization algorithms of the AI module.

More specifically, in FIG. 4, three dimension lesion 41 is located on the interior wall of a patient's colon or large intestine. During a colonoscopy examination, the endoscopist manipulates the proximal end of the colonoscope to redirect the camera at the distal tip of the colonoscope to image adjacent portions of the organ wall. In this way, video frames 42, 43, 44 and 45 are generated, each of which frames includes a partial view of lesion 41. Image frames I, I+1, I+2, I+3 are analyzed by partial lesion/feature detector AI module 46. Module 46 analyzes the partial views of the lesion in each of the multiple frames to determine whether the lesions are separate and unrelated or form part of a larger lesion, e.g., by matching up adjacent tissue boundaries in the various frames to piece together an aggregate image of the lesion. This aggregation process is concluded when, as indicated at step 47, feature boundaries in multiple images can be matched and stitched together with a degree of confidence greater than a threshold value to generate a reconstructed lesion. Techniques for matching features from adjacent video frames may include color matching, matching of adjacent tissue boundaries or tissue textures, or other techniques known to those of skill in the art of image manipulation. If during this assembly process the AI module determines, e.g., by disrupted boundary profiles, that one or more portions of the image whole is missing, the AI module may compute an estimate of the completeness of the image, and/or prompt the endoscopist to reposition the colonoscope to acquire additional image frames.

Once multiple frames of data are assemble to reconstruct a tissue feature, it is analyzed by feature detection algorithms of AI module 48, to generate a prediction and classification for the tissue feature or lesion. If the partial lesion/feature detector of the AI module indicates that additional image frames are required, the process of reconstructing and analyzing the data (now including additional image frames) is repeated, as described with respect to FIG. 2. By iteratively acquiring additional information that is presented in real-time or near real-time to the endoscopist, the ADR rate advantageously is expected to be improved. For example, a small tissue discoloration or polyp visible in a single frame might correspond to a benign growth. However, the ability of AI module 48 to detect and aggregate adjacent patches of similar tissue discoloration or pendunculations in successive video frames may result in a determination of a possibly malignant tumor, a much more critical determination for the endoscopist's consideration.

Figure 5:
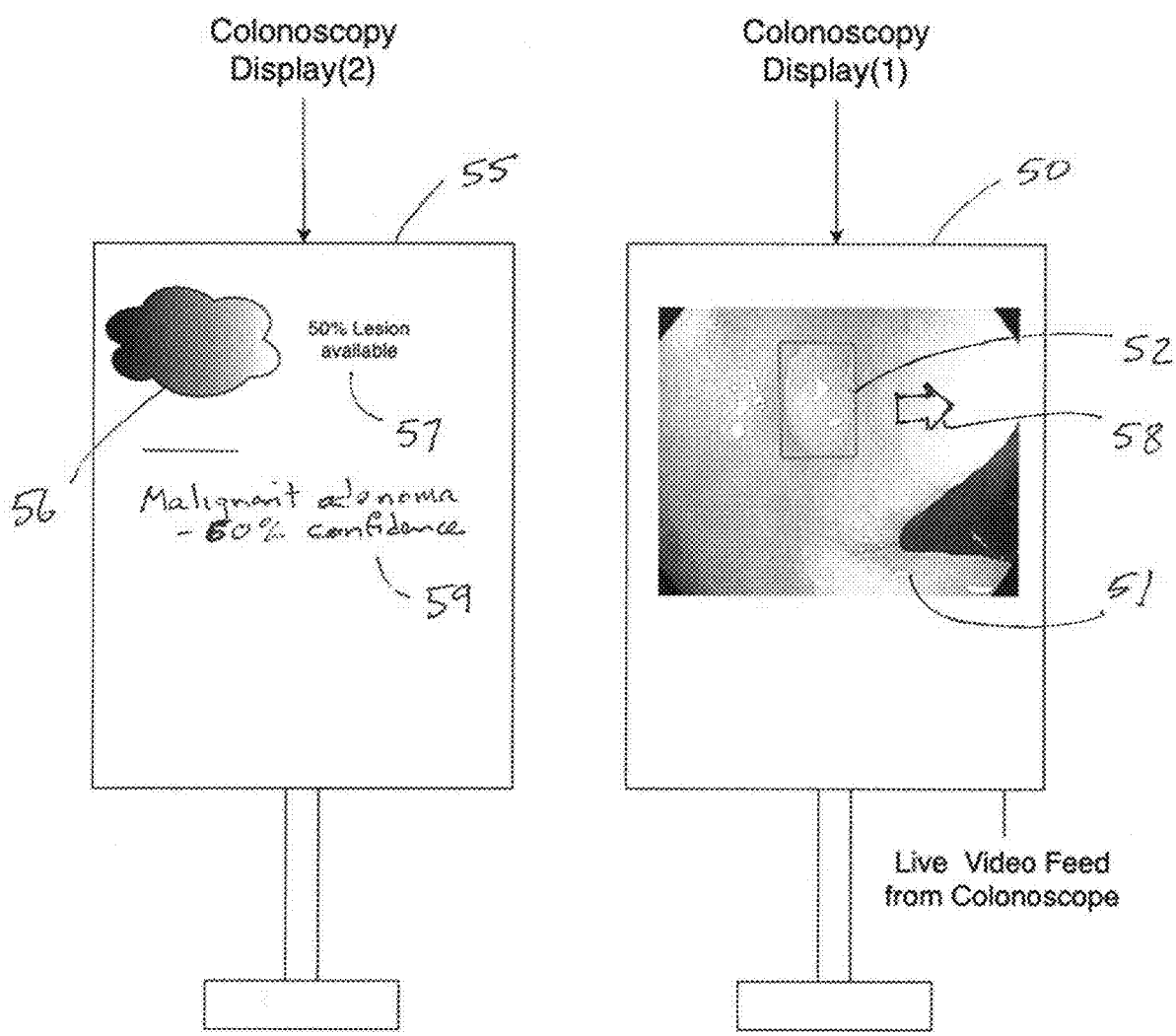
FIG. 5 is a schematic depicting a two display screen arrangement showing how an endoscopist might see the outcome on the monitor for a system employing the multiple frame AI module of the present invention.

Referring now to FIG. 5, an arrangement for displaying results of the present invention using two monitors is described. Monitor 50 is similar to the monitor of FIG. 3, and displays the real time image from the colonoscope 51 on which bounding box 52 is overlaid, indicating the presence of a potential lesion. If the entire lesion, as determined by the AI module, is not visible in the current video frame displayed on monitor 50, bounding box 52 is overlaid on as much the potential lesion is visible in the displayed video frame. In accordance with one aspect of the invention, second monitor 55 includes a display that may include a partial view of area of interest 56 and text 57 indicating the AI modules' estimate of the completeness of the area of interest. If the AI module determines that additional information is required to assess an area of interest, it may overlay arrow 58 on the real time video image 51 to prompt the endoscopist to obtain additional video frames in that direction.

In the alternative, or in addition, second monitor 55 may include as indicator of the completeness of the image acquisition, a progress bar, or other visual form of progress report, informing the endoscopist about the quality and quantity of data analyzed by the detection and characterization algorithms of the AI module. Second monitor 55 also may include a display including an updated textual classification of an area highlighted in bounding box 52, including a confidential level of that prediction based on the aggregated image data. For example, in FIG. 5, second monitor reports that the feature located within bounding box 52 is concluded by the AI module to be a malignant adenoma with 60% confidence, based on the estimated 50% of the lesion that is observable in the acquired video stream.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed:

1. A system for identifying tissue abnormalities in video data generated by an optical endoscopy machine, the endoscopy machine outputting real-time images of an interior of an organ as video frames, the system comprising:
    at least one video monitor operably coupled to the endoscopy machine to display the video frames output by the endoscopy machine;
    a memory for storing non-volatile programmed instructions; and
    a processor configured to accept the video frames output by the endoscopy machine and to store the video frames in the memory, the processor further configured to execute the non-volatile programmed instructions to:
        analyze a first video frame using artificial intelligence to determine if any part of a first tissue abnormality is visible within the first video frame, and if the first video frame is determined to include the first tissue abnormality, analyze adjacent video frames to locate other parts of the first tissue abnormality;
        generate a reconstructed image of the first tissue abnormality that spans the first video frame and adjacent video frames in which the other parts of the first tissue abnormality are located;
        analyze, using artificial intelligence, the reconstructed image to classify the first tissue abnormality;
        analyze the reconstructed image to estimate a degree of completeness of the reconstructed image;
        display on the at least one video monitor a bounding box surrounding a portion of the reconstructed image that is visible in a current video frame; and
        display on the at least one video monitor the estimate of the degree of completeness of the reconstructed image.

2. The system of claim 1, wherein the programmed instructions, when executed by the processor, generate the reconstructed image of the first tissue abnormality by aggregating at least one of the following in the first video frame and the adjacent video frames: a boundary of the first tissue abnormality, a color of the first tissue abnormality, and a texture of the first tissue abnormality.

3. The system of claim 1, wherein the programmed instructions, when executed by the processor, generate and display on the at least one video monitor a textual description of a type of the first tissue abnormality.

4. The system of claim 1, wherein the programmed instructions, when executed by the processor, provide that if analysis of the adjacent video frames does not locate other parts of the first tissue abnormality, the first video frame is analyzed using artificial intelligence to classify the first tissue abnormality and a bounding box is displayed on the at least one video monitor surrounding the first tissue abnormality.

5. The system of claim 4, wherein the programmed instructions, when executed by the processor, generate and display on the at least one video monitor a textual description of a type of the first tissue abnormality.

6. The system of claim 1, wherein the processor further is configured to execute the programmed instructions to:
    determine a direction of movement of a camera of the colonoscopy machines to acquire additional video frames for use in generating the reconstructed image; and
    display on the at least one video monitor an indicator of the direction of movement.

7. The system of claim 1, wherein the processor further is configured to execute the programmed instructions to:
    if analysis of the adjacent video frames detects a second tissue abnormality different from the first tissue abnormality, analyze the adjacent video frames to locate other parts of the second tissue abnormality.

8. The system of claim 1, wherein the programmed instructions, when executed by the processor, generate a reconstructed image of the first tissue abnormality by adding adjacent features extracted from the adjacent video frames to features extracted from the first video frame.

9. The system of claim 1, wherein the programmed instructions that implement the artificial intelligence includes a machine learning capability.

10. A method of identifying tissue abnormalities in video data generated by an optical endoscopy machine, the endoscopy machine outputting real-time images of an interior of an organ as video frames, the method comprising:
    acquiring the video frames output by the endoscopy machine;
    analyzing a first video frame using artificial intelligence to determine if any part of a first tissue abnormality is visible within the first video frame, and if the first video frame is determined to include the first tissue abnormality, analyzing adjacent video frames to locate other parts of the first tissue abnormality;
    generating a reconstructed image of the first tissue abnormality that spans the first video frame and adjacent video frames in which the other parts of the first tissue abnormality are located;
    determining a direction of movement of a camera of the colonoscopy machines to acquire additional video frames for use in generating the reconstructed image;
    analyzing, using artificial intelligence, the reconstructed image to classify the first tissue abnormality;
    displaying on at least one video monitor the real time images from the endoscopy machine and a bounding box surrounding a portion of the reconstructed image that is visible in a current video frame; and
    displaying on the at least one video monitor an indicator of the direction of movement.

11. The method of claim 10, wherein generating the reconstructed image of the first tissue abnormality comprises aggregating at least one of the following in the first video frame and the adjacent video frames: a boundary of the first tissue abnormality, a color of the first tissue abnormality, and a texture of the first tissue abnormality.

12. The method of claim 10, further comprising generating and displaying on the at least one video monitor a textual description of a type of the first tissue abnormality.

13. The method of claim 10, further comprising, if analysis of the adjacent video frames does not locate other parts of the first tissue abnormality:
    analyzing the first video frame using artificial intelligence to classify the first tissue abnormality; and
    displaying a bounding box on the at least one video monitor surrounding the first tissue abnormality.

14. The method of claim 13, further comprising generating and displaying on the at least one video monitor a textual description of a type of the first tissue abnormality.

15. The method of claim 10, further comprising:
    analyzing the reconstructed image to estimate a degree of completeness of the reconstructed image, and
    displaying on the at least one video monitor the estimate of the degree of completeness of the reconstructed image.

16. The method of claim 10, further comprising, if analysis of the adjacent video frames detects a second tissue abnormality different from the first tissue abnormality, analyzing the adjacent video frames to locate other parts of the second tissue abnormality.

17. The method of claim 10, further comprising generating a reconstructed image of the first tissue abnormality by adding adjacent features extracted from the adjacent video frames to features extracted from the first video frame.

18. The method of claim 10, further comprising implementing the artificial intelligence to include a machine learning capability.

* * * * *